US00PP15595P3

(12) United States Plant Patent
Shahi et al.

(10) Patent No.: US PP15,595 P3
(45) Date of Patent: Mar. 1, 2005

(54) ***CYMBOPOGON* PLANT NAMED 'RLJCC1'**

(50) Latin Name: *Cymbopogon commutatus*
Varietal Denomination: RLJCC1

(75) Inventors: Ashok Kumar Shahi, Jammu (IN); Satya Narayan Sharma, Jammu (IN); Swadesh Pal, Jammu (IN); Suresh Chandra, Jammu (IN); Prabhu Dutt, Jammu (IN); Surendra Singh Balyan, Jammu (IN); Maharaj Krishen Bhan, Jammu (IN); Subhash Chandra Taneja, Jammu (IN); Ravinder Kumar Raina, Jammu (IN); Vijeshwar Verma, Jammu (IN); Shazia Zahoor, Jammu (IN); Maharaj Krishen Kaul, Jammu (IN); Ghulam Nabi Qazi, Jammu (IN)

(73) Assignee: Council of Scientific and Industrial Research, New Delhi (IN)

( * ) Notice: Subject to any disclaimer, the term of this patent is extended or adjusted under 35 U.S.C. 154(b) by 164 days.

(21) Appl. No.: 10/067,808

(22) Filed: Feb. 8, 2002

(65) Prior Publication Data

US 2003/0154532 P1 Aug. 14, 2003

(51) Int. Cl.[7] ..... A01H 5/00
(52) U.S. Cl. ..... Plt./386
(58) Field of Search ..... Plt./386

*Primary Examiner*—Anne Marie Grunberg
*Assistant Examiner*—June Hwu
(74) *Attorney, Agent, or Firm*—Burns, Doane, Swecker & Mathis L.L.P.

(57) ABSTRACT

A new and distinct variety of *Cymbopogon commutatus* grass is provided. The new variety was discovered during a mass selection program that was carried out in India in a cultivated area, and offers significant advantages over a typical plant of the species. More specifically, the new variety exhibits superior drought tolerance, a vigorous perennial growth habit, and lighter green leaves than typically exhibited by the species. The plant produces an essential oil having an enhanced geraniol and geranyl acetate content that is useful to form perfumes and in flavor applications. Asexual reproduction can be readily carried out by the rooting of slips.

11 Drawing Sheets

Botanical/commercial classification: *Cymbopogon commutatus*/Cymbopogon Plant.
Varietal denomination: cv. 'RLJCC1'.

FIELD OF THE INVENTION

The present invention relates to a drought tolerant variety of *Cymbopogon commutatus* plant that is rich in geraniol and geranyl acetate named 'RLJCC1'.

BACKGROUND OF THE INVENTION

The Indian sub-continent has a rich genetic diversity in aromatic plants. The aromatic grasses such as *Cymbopogon* and *Vetiveria zizanoides* have been used by man from ancient times both for medicine and perfumery. The genus *Cymbopogon*:, belonging to family Poaceae, is a rich source of aroma chemicals, especially terpenoids. These chemical compounds are present in varying concentrations in *Cymbopogon* and are used widely in perfumery, and in the flavor and pharmaceutical industries. There are up to 60 species of *Cymbopogon* native to the tropical and sub-tropical regions of Africa and Asia. See, Corrigan, D. (1992), "Adverse Effects on Herbal Drugs", vol. I, Springler verlag, Berlin, pages 115–123. Out of 27 species available in India, mainly *C. flexuosus, C. winterianus* and *C. martinii*, var. 'Motia' have been exploited for commercial cultivation as a source of citral, citronellal and geraniol respectively. *Cymbopogon commutatus* is surviving in the sub-tropical environment of the Jammu District near R. S. Pura Tehsil, India. A massive collection of this plant was made in India during 1994.

The occurrence of *Cymbopogon commutatus* is reported in Sudan Banthorpe, D.V., Duprey, R. J. H., Hassan, M., Janes, J. F. and Modawi, B. M (1976) *Planta Medica*

29:10–19. Such plant also is present in Pakistan, Somalia, Tanzania, Iraq, and Northern India. See, Nasir, E. and Ali, S.I. (1982), "Flora of Pakistan—Poaceae", No. 143, University of Karachi, Karachi, Pakistan.

India's share in land resources of the world is only 2% on which 18% of the world's population and 15% of the world's livestock survive. The geographical matrix of India based on the reported area of 305.01 million hectares is broadly grouped into three sectors—the agriculture sector (59.27%), the ecological sector (33.56%), and the non-agricultural sector (7.17%). See, Prasad, R. N. and Biswas, P.P. (2000), "Land resource in sustainable agricultural development—issues and strategies Indian Farming", 49(11): Pages 9–13. Dryland agriculture in India is now practiced on 100 million hectares or 70% of the total arable land of 143.8 million ha. Crop production on these lands is dependent entirely on natural precipitation. This information suggests that there is need in India and elsewhere to develop an improved drought tolerant variety of *C. commutatus*.

Present annual demand of geraniol in India stands at about 100 tonnes which is likely to increase during the coming years. In India the current production is only 50 tonnes/year. The geraniol containing oil can be used for imparting an aroma to the wide range of perfumery products.

The Polymerase Chain Reaction (PCR) technique has found wide use in molecular biology. Recent advances in PCR have made this technique one of the most powerful tools for a wide spectrum of molecular analyses, such as genome mapping. See, Benito C., Figueiras, A. M., Zaragoza, C.,Gallego, F. J., and De la Pena, A., (1993), Plant Mol. Biol., 21:181–183; molecular evolution, Brown, P. T. H., Lange, F. D., Kranz, E, and Lorz, H., (1993), Mol. Gen. Genet., 237:311–317; gene tagging; molecular taxonomy;

diagnosis of genetic diseases, and forensic sciences, Erlich, H. A. D., Gelfand and J. J. Sninsky (1991), Science 252: 1643–1651. Randomly Amplified Polymorphic DNA profiling (RAPD) is one of the PCR techniques which is an amplification-based nucleic acid scanning technique driven by synthetic oligodeoxynucleotide primers of arbitrary sequence producing characteristics DNA fingerprints capable of detecting sequence polymorphism in anonymous nucleic acid templates. In this technique the amplification of genomic DNA using random short primers results in multiple amplification products representing amplicons randomly distributed throughout a genome which can be resolved by agarose gel electrophoresis and visualized by ethidium bromide staining.

The polymorphism obtained using RAPD results from point mutations, insertions, deletions, and inversions occuring in the respective genomes over time. These are usually dominant markers that are inherited in simple Mendelian fashion. No references, however, are known to exist on the RAPD analysis of *Cymbopogons*. The methodology used by D.Godwin, N.Sangduen, R.Kunanuvatchaidach, G.Piprridis, and S. W. Adkins (1996), Plant Cell Reports, 16: 320–324; Taku Ohmori, Minoru Murata and Fusao Motoyoshi (1995), Jpn. J. Genet. 70; 179–184; F. N. Wachira, R. Waugh, C. A.Hackett, and W. Powell (1994), Genome 38: 201–210, has been used for the present studies to further confirm the distinctiveness of the new variety of the present invention.

A well-established method of mass selection for developing an improved variety from the wild collection of *Cymbopogon commutatus* was initiated during 1994 and individual plant progenies were raised vegetatively by slips in a cultivated area tended by man.

Similar appearing uniform progenies having the desired phenotypic characters, e.g., an improved tiller character, high rate of tillerization, fresh herbage, essential oil content (%), and oil quality indices (ratio of geraniol/geranyl acetate to citral) were bulked for seed formation.

Seed raised progenies exhibited phenotypic variations. A single plant of desired characters ultimately was selected and was further multiplied vegetatively. This plant of the present invention was designated 'RLJCC1'. Studies and selection were continued from 1995 to 1999 for the evaluation of essential oil quality stability (i.e., geraniol and geranyl acetate) and drought tolerance.

The primary object of the present invention was to develop new *Cymbopogon commutatus* variety capable of growing under natural drought conditions.

Another object of the present invention was to develop a new *Cymbopogon commutatus* variety whcih exhibits the presence of geraniol and geranyl acetate as major chemical constituents and having a low citral content for applications in the perfumery and flavor industries.

Yet another object of the present invention was to develop to a new *Cymbopogon commutatus* variety useful in the marginal as well as in waste lands for the production of geraniol and geranyl acetate as well as ocimene.

SUMMARY OF THE INVENTION

It was found that the new *Cymbopogon commutatus* variety of the present invention exhibits the following combination of characteristics:

(a) displays a perennial vigorous growth habit, (b) commonly forms lighter green leaves than typically exhibited by the species, (c) forms an abundance of roots with superior tillering, (d) displays superior drought tolerance, (e) produces essential oil having an enhanced geraniol and geranyl acetate content, and (f) readily undergoes asexual reproduction by the use of slips.

BRIEF DESCRIPTION OF THE DRAWINGS AND PHOTOGRAPHS

The accompanying drawings and photographs provide information concerning the inherently exhibited characteristics of the new 'RLJCC1' variety. In some instances information is provided for comparative purposes with respect to the typical *Cymbopogon commutatus* plant from which the new 'RLJCC1' variety was selected and the *Cymbopogon nardus* 'RRL-CN5' variety (non-patented in the United States). The depicted plants were being grown in the field at the Jammu and Kashmir State of North India at a longitude 75°55'E, latitude 32°44N. Such plants were reproduced by the rooting of cuttings. Slips were planted in February and flowering began in April and continued to the $5^{th}$ and $6^{th}$ leafing stage during May and June.

Figure 10:
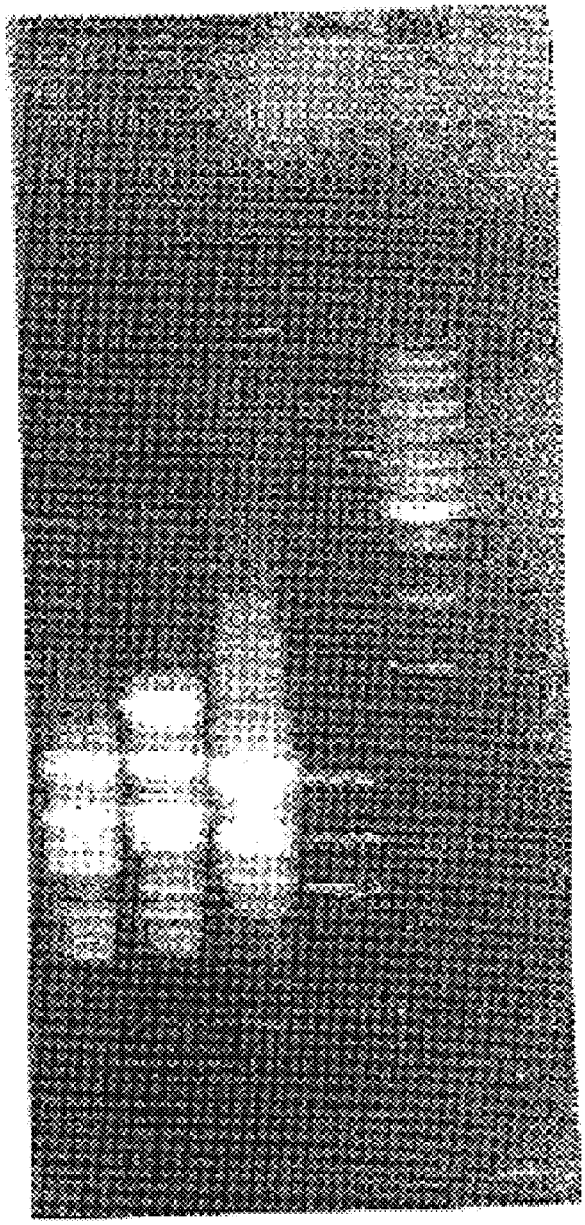

FIG. 10 depicts the RAPD profile of the new 'RLJCC1' variety and of the 'RRL-CN5' variety of *Cymbopogon nardus* using two different primers (i.e., 27 and 29). Lane 1 shows the 'RLJCC1' variety and Lane 2 shows the 'RRL-CN5' variety using primer 27 (48 ng) and a $MgCl_2$ concentration of 2.5 mM. Lane 3 shows the 'RLJCC1' variety and Lane 4 shows the 'RRL-CN5' variety using primer 29 (33 ng) and a $MgCl_2$ concentration of 2.5 mM.

Figure 11:
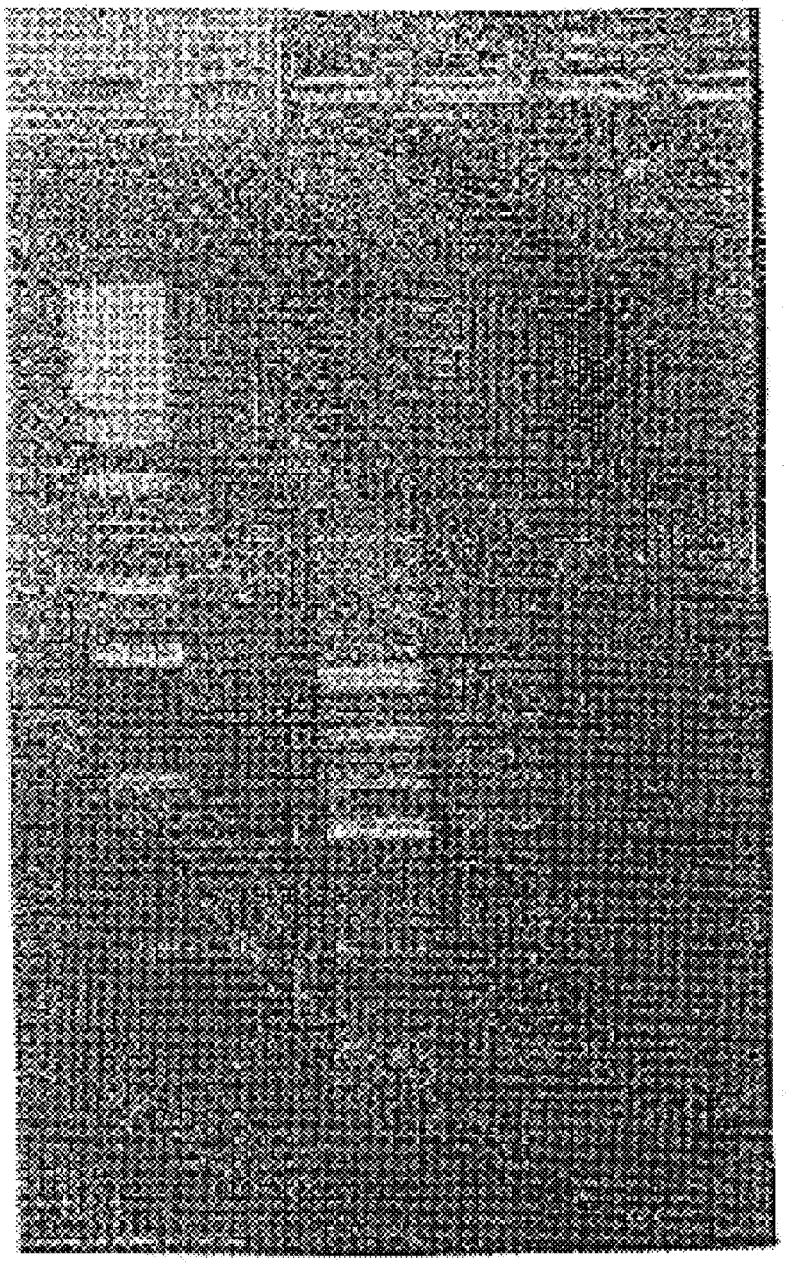

FIG. 11 depicts the RAPD profile of the new 'RLJCC1' variety and of the 'RRL-CN5' variety of *Cymbopogon nardus* using primer 22 (33 ng) and a $MgCl_2$ concentration of 2.5 mM. Lane 3 shows the 'RLJCC1' variety and Lane 4 shows the 'RRL-CN5' variety.

THE *Cymbopogon* GENUS

*Cymbopogon* is recognized to be closely allied to *Andropogon* and *Hyparrhenia* and it is sometimes quite difficult to distinguish them. A useful diagnostic character is the aromatic flavor when a leaf of *Cymbopogon* is chewed with the other genera being tastless. The genus is notorious for the considerable variations within species and the weak separation between species. Consequently the taxonomy is still in a fluid state with differing opinions about the level at which specific rank should be accorded and with many of the species based upon indefinite characters of little practical diagnostic value.

Plants of the *Cymbopogon* genus commonly are tall robust perennials, the leaf blades are linear, aromatic, and the lingules are membranous or scarious. The inflorescence is composed of paired racemes borne on a short common peduncle and is enclosed by a boat-shaped spatheole and densely crowded into a leafy flase panicle which is often very large and complex, raceme are short, with each raceme base being deflexed at maturity, the lower most pair of spikelets in each raceme is homogamous, and the internodes and pedicels are linear. Sessile spikelets are dorsally compressed, callus is obtuse inserted in the concave, the lower ligule is streaked with oil glands, two-keeled, and the lower florets are reduced to a hyaline lemmma with awn from the sinus. Pedicelled spikelets caryopsis are oblong.

*CYMBOPOGON COMMUTATUS* (STEUD.)STAPF

This species can be generally described as indicated hereafter.

Perennial, culms erect 15 to 150 cm high, leaf blade flat 10–50 cm long, 1–4 mm wide, dull green narrowed at the base, filiform tip, basal sheaths persistent thinly pubescent, spatheoles narrowly lanceolate to narrowly elliptic, 2–2.6 cm long. Racemes 15–40 mm long, lower most pedicel swollen and barrel-shaped internodes and pedicels densely ciliate along the margins glabrous to minutely puberulous on the back. Sessile spikelets narrowly lanceolate 4–7 mm long, lower glume flattish to deeply concave on the back. Upper lemma deeply bifid, with an awn 10–20 mm long. Chromosome number 2n=20, 40, Nasir, E. and Ali, S. I. (1982), Flora of Pakistan—Poaceae, No. 143, University of Karachi, Karachi, Pakistan.

DETAILED DESCRIPTION OF THE NEW VARIETY

The plants described were grown in the field at the Jammu and Kashmir State of North India. Slips were planted February. Leafing and tillerization started during March with the rise in ambient temperature, and flowering began in April and continued to the $5^{th}$ and $6^{th}$ leafing stage during May and June.

Color is specified by reference to the Methum Handbook of Colours by A. Kornerup and J. H. Wanscher, revised by Don Parey, Third Edition (1978), published by Erye Methuen, London, except where otherwise indicated.

The asexual reproduction achieved by the planting of slips and the rooting of cuttings in experimental fields of the Regional Research Laboratory, Jammu, Jammu and Kashmir State, North India, has confirmed that the combination of characteristics of the new 'RLJCC1' variety are firmly fixed. Such characteristics are transmitted true to type to subsequent generations.

The new variety of the present invention can be readily distinguished from its mother plant of the *Cymbopogon commutatus* species. More specifically, the 'RLJCC1' variety displays lighter green leaves, is more drought tolerant and inherently produces a more advantageous essential oil having an enhanced geraniol and geranyl acetate content.

The new variety when fully mature commonly achieves a maximum height of approximately 100 to 150 cm. The canopy spread of the plant commonly is approximately 50 cm, and the basal area of a mature plant commonly is approximately 960 $cm^2$.

Figure 4:
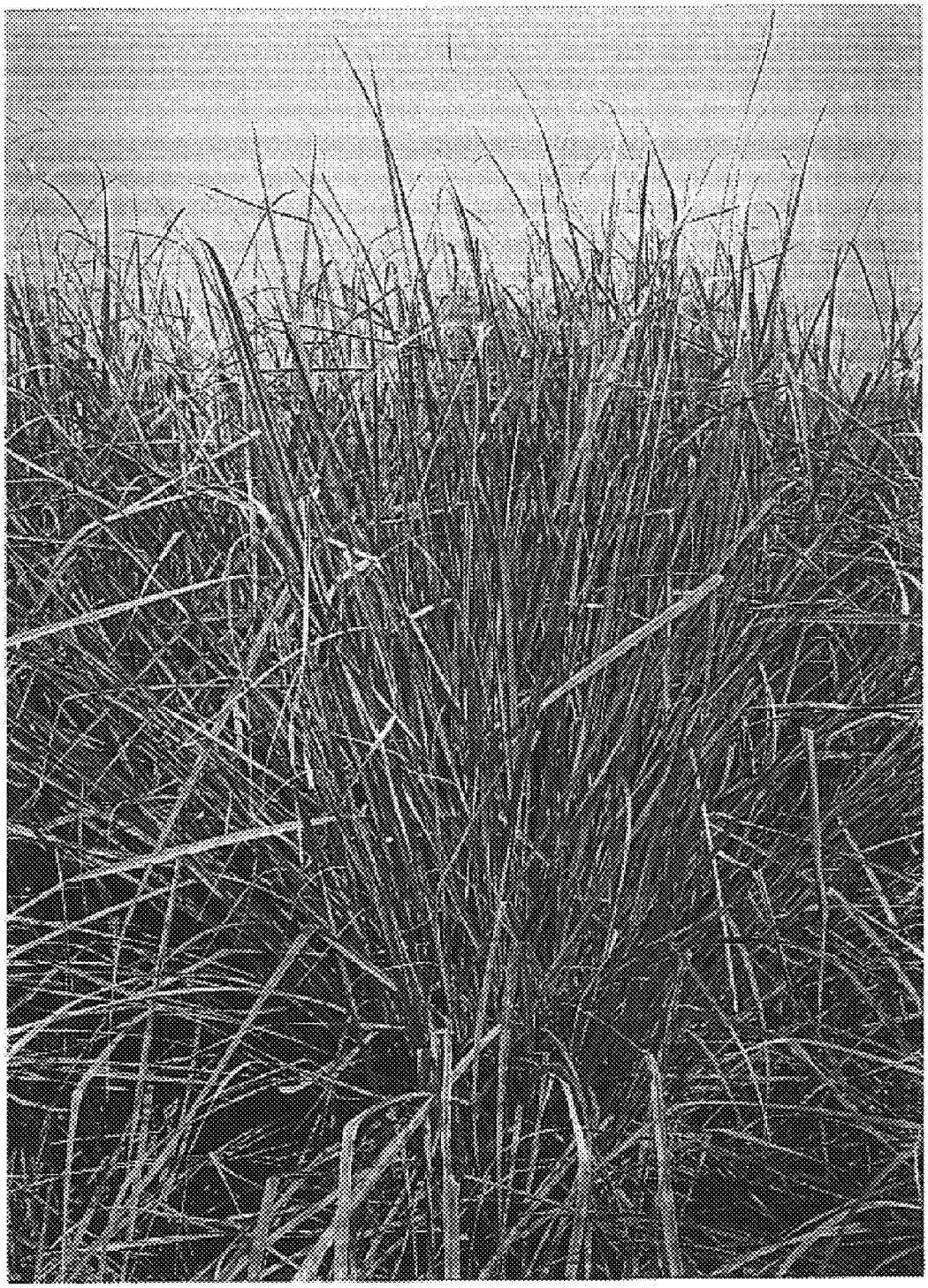
FIG. 4 depicts a typical plant of the 'RLJCC1' variety at the vegetative growth stage of development.
Figure 5:
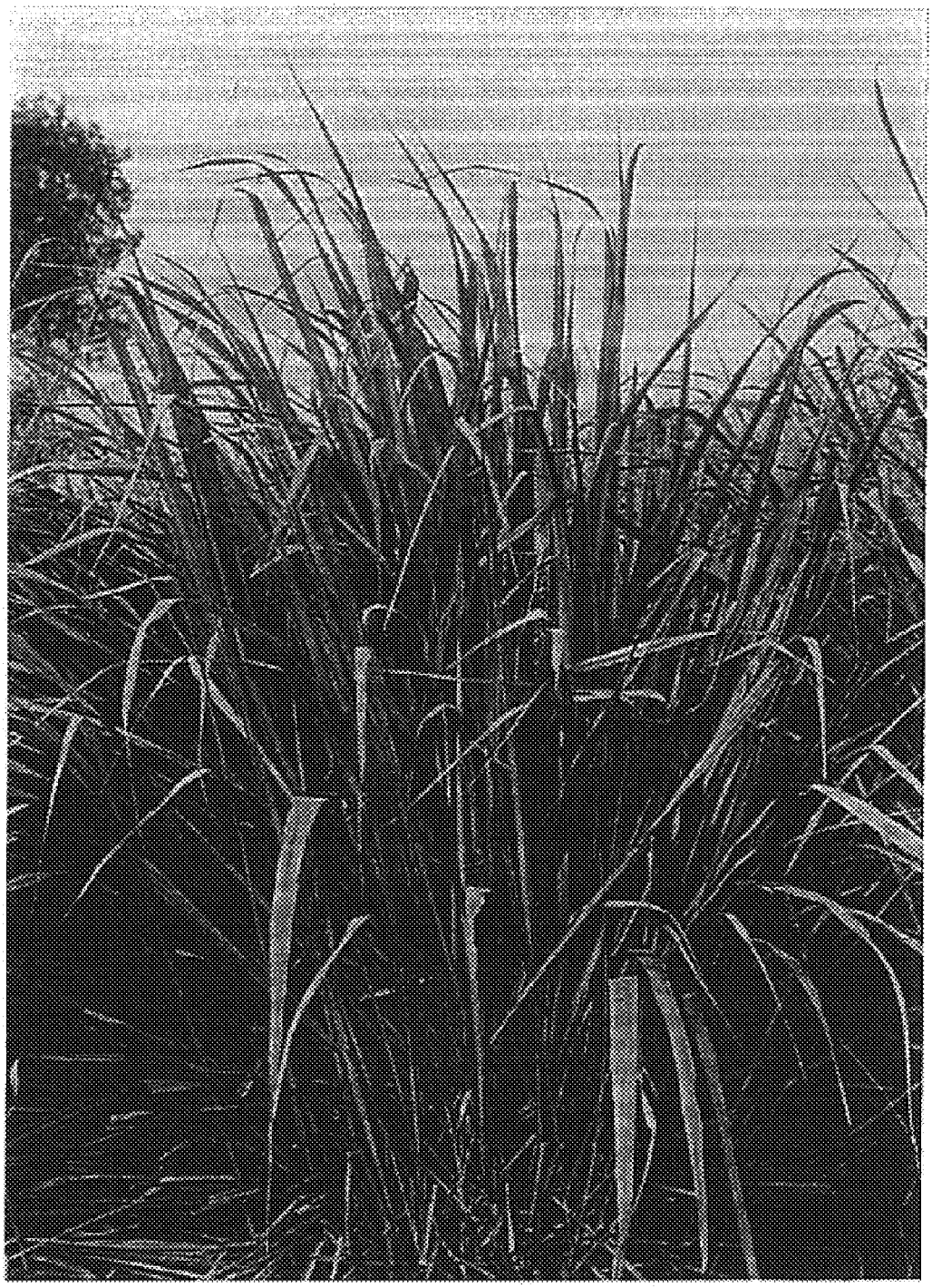
FIG. 5 depicts for comparative purposes a typical *Cymbopogon commutatus* plant at the vegetative growth stage of development from which the new 'RLJCC1' variety was obtained through selection. Note the dark green coloration of the leaves.
Figure 6:
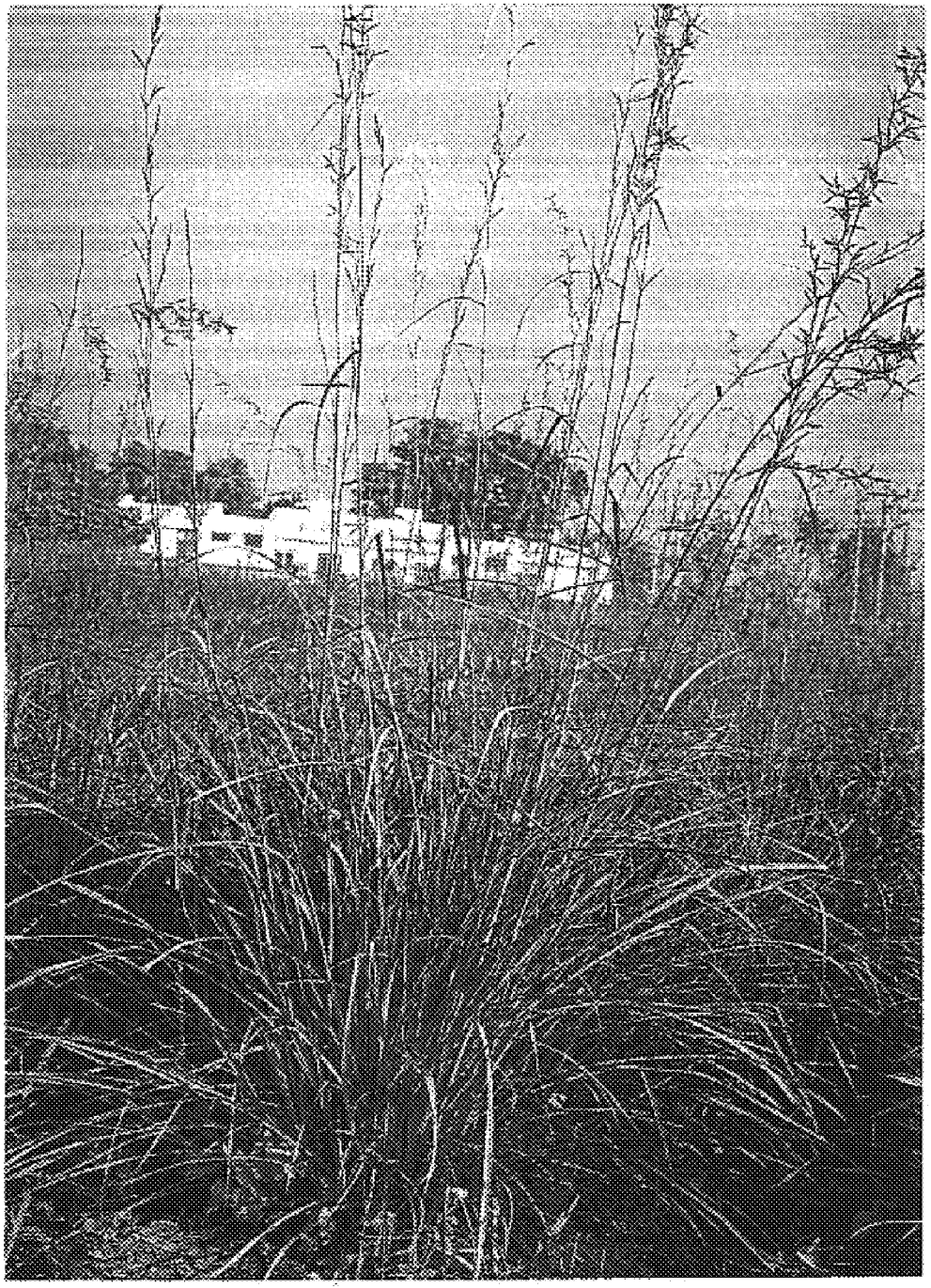
FIG. 6 depicts a further view of typical plant of the 'RLJCC1' variety following seed production.
Figure 7:
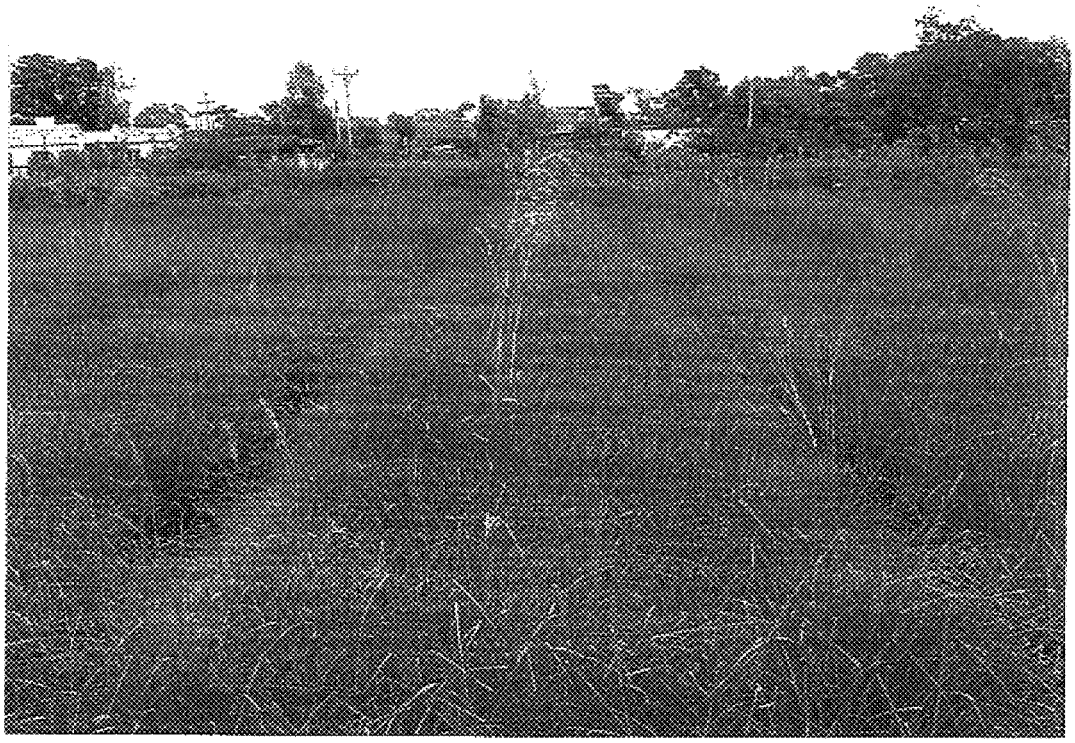
FIG. 7 depicts a mass primarily of plants of the 'RLJCC1' variety while growing in the field at the early vegetative stage of development.
Figure 8:
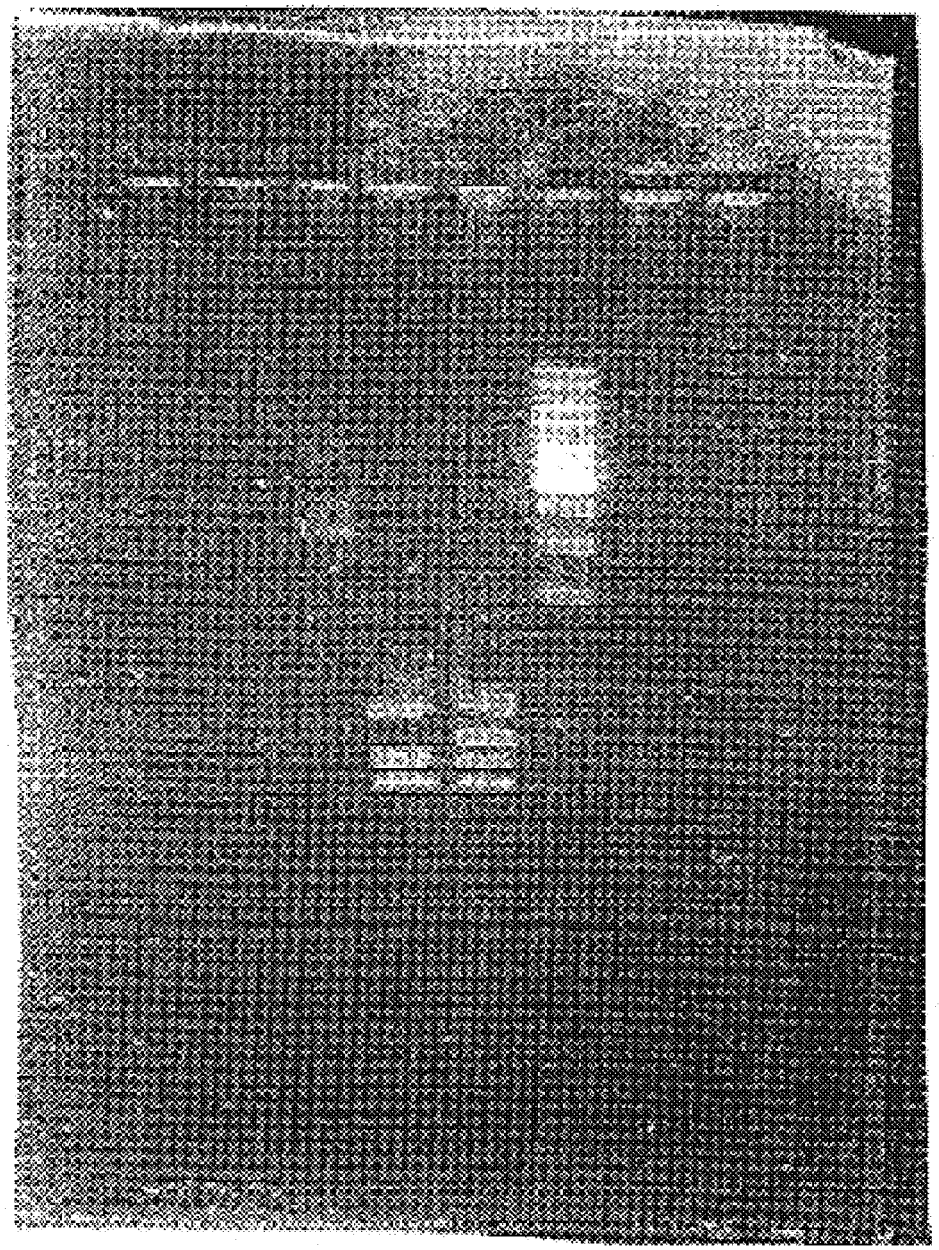
FIG. 8 depicts the RAPD profile of the new 'RLJCC1' variety and the typical *Cumbopogon commutatus* plant (Lanes 3 and 4 respectively) using primer 22 (48 ng) and a $MgCl_2$ concentration of 2.5 mM.
Figure 9:
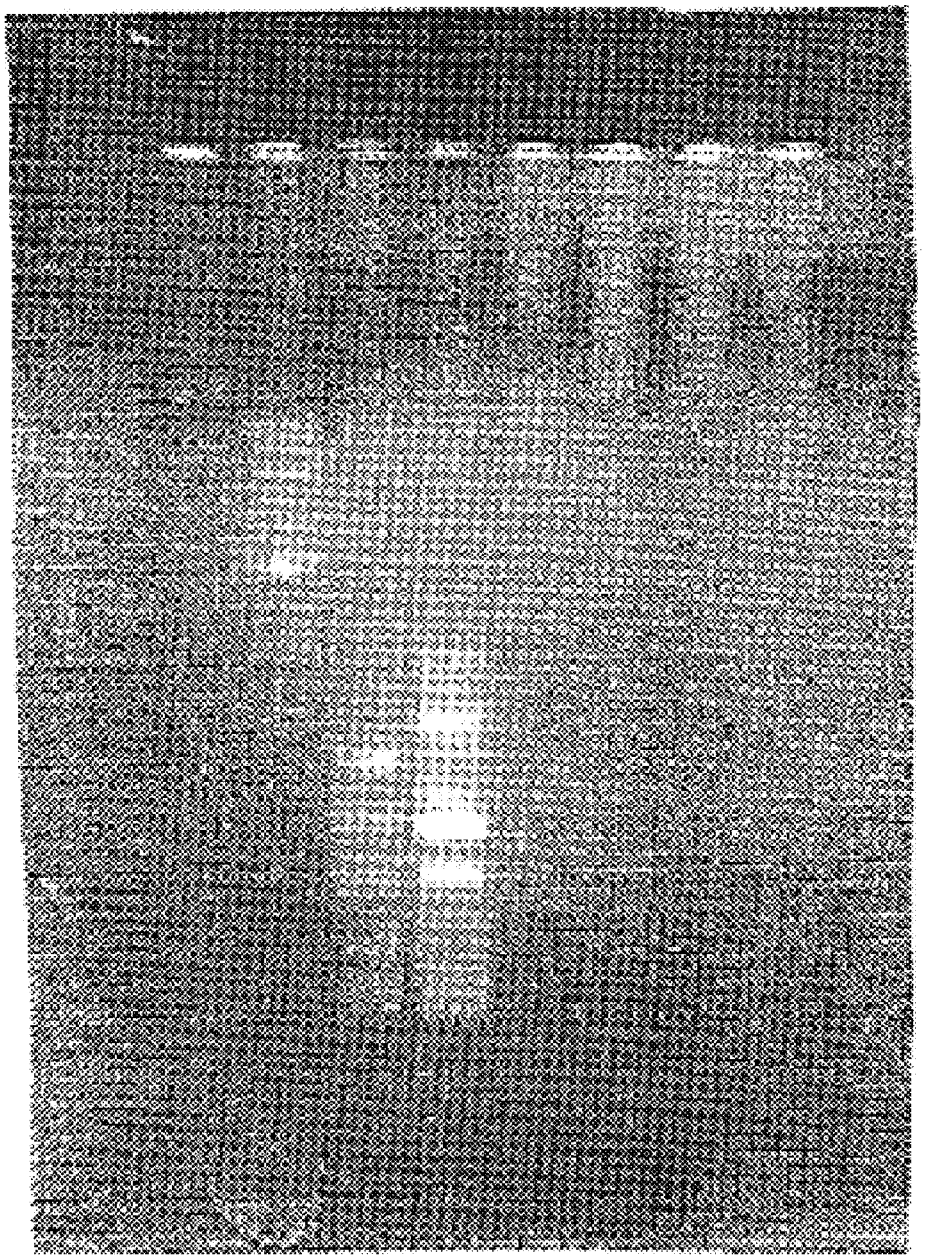
FIG. 9 depicts the RAPD profile of the new 'RLJCC1' variety and the typical *Cymbopogon commutatus* plant (Lanes 3 and 4 repectively) using primer 27 (48 ng) and a $MgCl_2$ concentration of 2.5 mM.

The upper surface of the leaf blade is 30D5 in coloration. This can be compared to a coloration of 27E5 typically displayed by the mother plant of *Cymbopogon commutatus*. Stated differently the leaves of the species commonly are dull jade green as shown in FIG. 5, while the leaves of the 'RLJCC1' variety are a lighter green as shown in FIG. 4. The coloration of under surface of the leaves of 'RLJCC1' is 27E5. The leaf margin is entire and leaf surface is smooth on the upper surface and somewhat rough on the under surface. The leaf blade is flat and linear and commonly measures approximately 50 cm in length. The leaf blade width commonly is approximately 5 to 8 mm at the widest point. The leaf apex is filiform. The leaf sheath commonly is approximately 5 to 7 cm in length, relatively wide, long persistent, glabrous, possesses a smooth surface texture and is straw yellow (3B4) in coloration.

The culms commonly are approximately 30 to 50 cm in length and approximately 4 to 5 mm in width. Their texture is smooth and the coloration is Timber Green, 6H, Plate 18 by reference to "A Dictionary of Color" by A. Maerz and M. Reapaul, Second Edition (1950) by McGraw Hill Book Company of New York.

Figure 1:
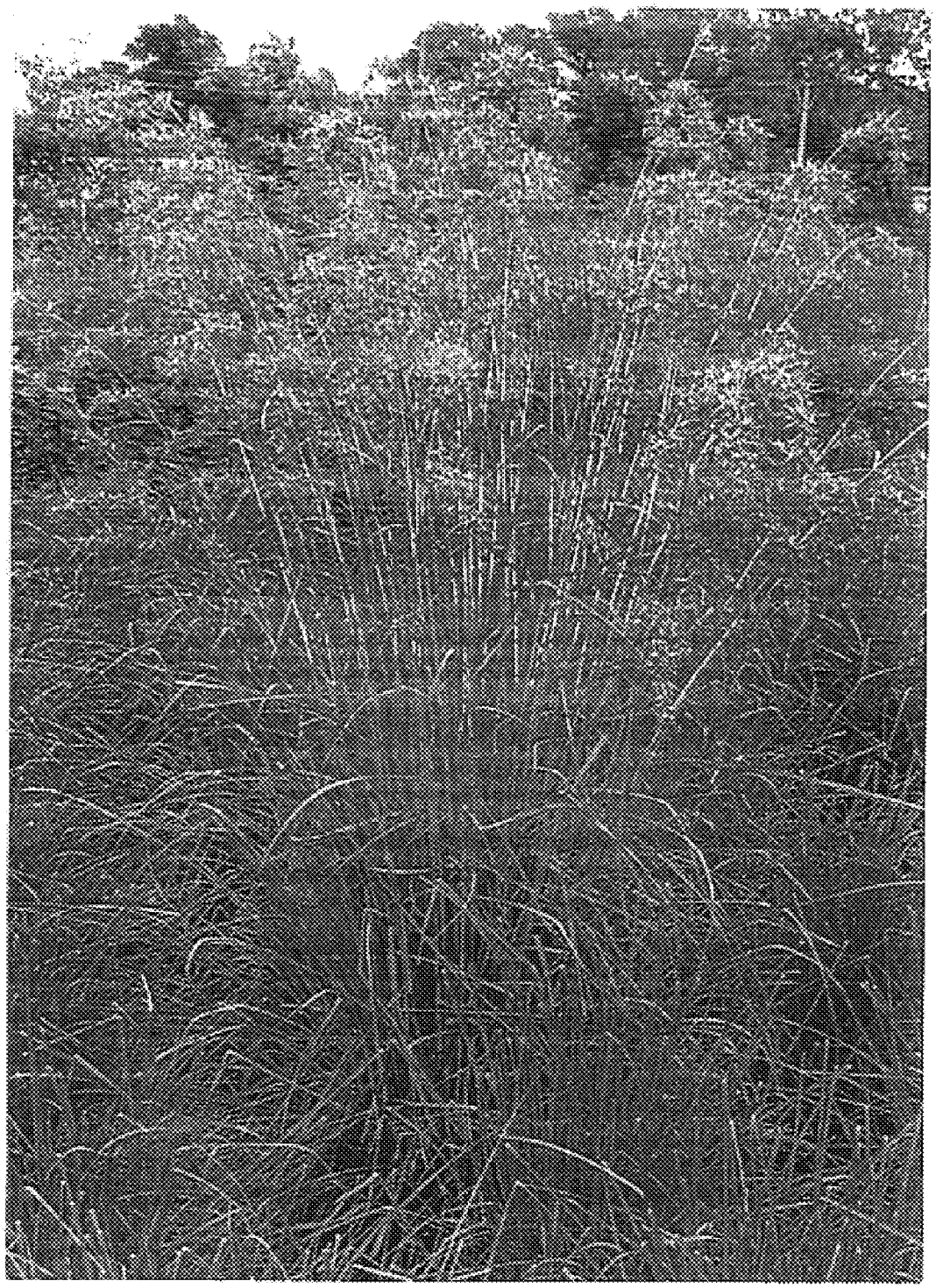
FIG. 1 depicts a typical plant of the 'RLJCC1' variety while displaying a profusion of inflorescence-bearing shoots.
Figure 2:
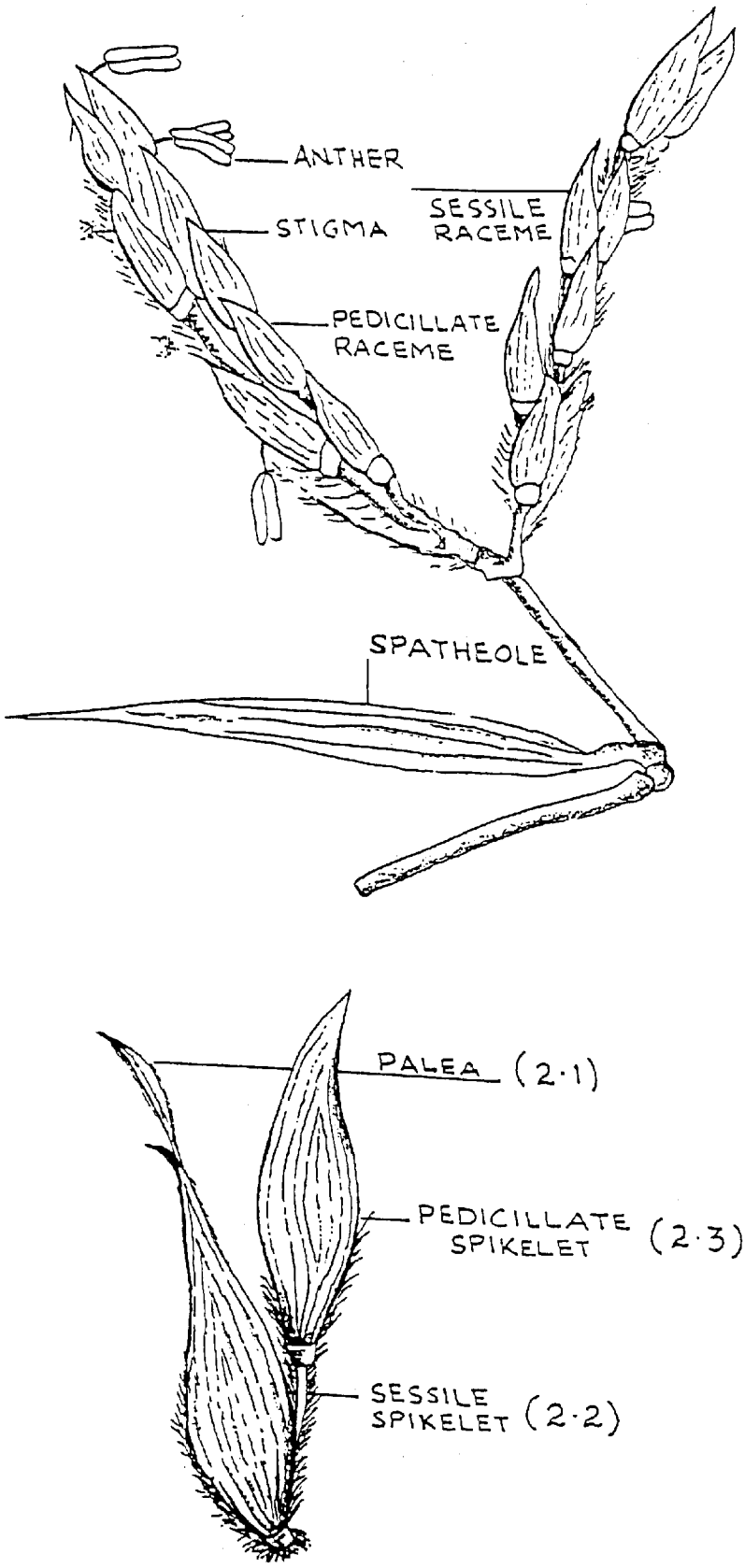
FIG. 2 illustrates in detail typical sessile and pedicillate spikelets of the inflorescence of the 'RLJCC1' variety.
Figure 3:
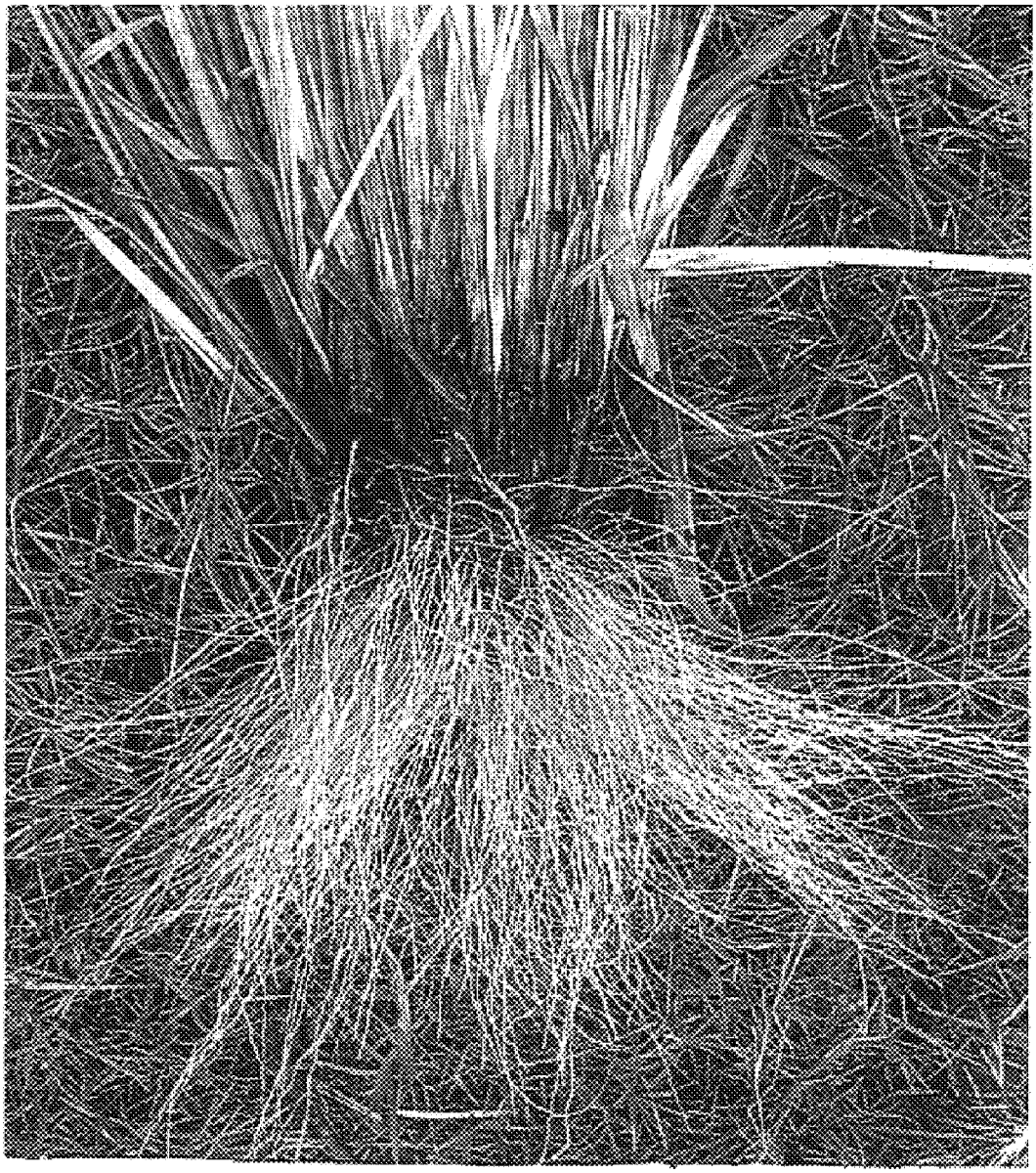
FIG. 3 depicts a close view of the typical adventitious root system of the 'RLJCC1' variety.

An extensive highly branched rooting system is formed as illustrated in FIG. 3. The primary root is divided into many fibrous branches that commonly display a coloration of light brown, 1A, Plate 18 by reference to "A Dictionary of Color". A root length of approximately 10 to 15 cm commonly is observed.

Commonly 10 to 12 nodes are present with 1 to 3 lateral branches at each node.

The ligules are yellowish-grey (3B2) in coloration, scarious, rotundate, and measure approximately 4 to 5 mm.

The inflorescence commonly appears in March–April and September–October. A synchronous mass flowering pattern is observed. A spatheate panicle of paired divariate racemes is formed having a length of approximately 50 to 100 cm. The color is near grey, 1E18.

The spikelets commonly are 4 to 5 mm in length, sessile, are linear-lanceolate, acuminate, as well as pedicelled in pairs. The pedicels are villous and the spathes are approximately 1.5 to 3 cm in length.

The glume is boat-shaped, pilose on the back, the base margin is ciliate, the lower lemma hyaline linear-lanceolate, and the upper lemma is hyaline. The awn is slender, typically is approximately 12.6 mm in length, and geniculate, and there are two lodicules. A typical palea commonly measures approximately 5.6 mm and a typical lemma commonly measures approximately 4.3 mm.

The anthers are three in number, dithecous, extrose and versatile. The stigma is deep red in color (11C8), is unilocular and superior globose with one basal ovule and two feathery stigmas elevated on two separate styles. A typical ovary commonly is approximately 0.2 mm in size and dull yellow (3A3) in coloration.

The seeds are oblong, approximately 1 mm in size, plano-convex in configuration, and new cocoa natal brown in coloration, from Plate 7, Row 10 Column A of "A Dictionary of Color" by A. Maerz and R. Reapaul.

During observations to date the pest and disease resistance/susceptibility is believed to be comparable to that of the species.

The quantity of essential oil produced by the new 'RLJCC1' variety is believed to be generally comparable to that of the species. However, the content of the essential oil is considered to be superior to that of the species with more geraniol and geranyl acetate being present. Also, the citral content of the essential oil was lower than that commonly displayed by the species.

In following Table 1 the essential oil content of the new 'RLJCC1' variety and the typical mother plant of *Cymbopogon commutatus* are compared.

TABLE 1

| | Percentage of | | | | |
|---|---|---|---|---|---|
| Plant | Geraniol | Geranyl acetate | Total of geraniol and geranyl acetate | Citral | Essential oil Content (%, w/w) on fresh weight basis |
| Mother plant | 34.40 | 28.00 | 62.40 | 18.33 | 0.4–0.5 |
| 'RLJCC1' | 74.50 | 9.20 | 83.70 | 5.0 | 0.45–0.5 |

It will be noted that the combined geraniol and geranyl acetate content of the essential oil of the 'RLJCC1' variety exceeds 80 percent by weight. The citral content in this instance was only 3.0 percent by weight.

The drought tolerance performance of the new 'RLJCC1' variety has been found to be superior to that commonly exhibited by the species and by the related *Cymbopogon nardus*, var. 'RRL-CN5'. Drought tolerance observations are summarized in the following Table 2.

TABLE 2

| Plant | Drought Tolerance Value (%) |
|---|---|
| *Cymbopogon Commutatus* 'RLJCC1' | 12 |
| *Cymbopogon Commutatus* | 10.5 |
| *Cymbopogon nardus* var. 'RRL-CN-5' | 9 |

When the new 'RLJCC1' variety was grown in a large scale field trial and compared to typical *Cymbopogon commutatus* and to 'RRL-CN5' variety, the comparative data presented in Table 3 was observed.

TABLE 3

| | Plant | | |
|---|---|---|---|
| Parameter | 'RLJCCI' | *C.commutatus* | 'RRL-CN-5' |
| Plant height (to flowering tip) (cm) | 104 | 109 | 115 |
| Number of tillers per plant | 66 | 30 | 40 |
| Rate of tillerization | 2.0 | 1.8 | 1.9 |
| Survival of plants (%) | 85 | 75 | 80 |
| Herbage/plant (g) (Semi-Dry) | 175 | 170 | 200 |
| Number of leaves | 159 | 152 | 150 |

TABLE 3-continued

| | Plant | | |
|---|---|---|---|
| Parameter | 'RLJCCI' | *C.commutatus* | 'RRL-CN-5' |
| Leaf length (cm) | 50 | 48 | 60 |
| Leaf width (mm) | 68 | 65 | 65 |
| Essential oil content (% w/w) | 0.45 | 0.40 | 0.45 |
| Essential oil production in liters per hectare | 78.8 | 75.0 | 80.0 |

The RAPD profiles of the 'RLJCC1' variety, its *Cymbopogon commutatus* mother plant, and the 'RRL-CN5' variety using the primers identified in Table 4 can be used to distinguish the specific cultivars/chemotypes.

TABLE 4

| Primer code | Operon Random primer | Primer sequence | Sequence I.D. |
|---|---|---|---|
| 22 | OPA02 | 5'-TGCCGAGCTG-3' | 1 |
| 27 | OPA07 | 5'-GAAACGGGTG-3' | 2 |
| 29 | OPA09 | 5'-GGGTAACGCC-3' | 3 |

See in this regard the results reported in FIGS. 8 to 11.

92–95° C.– 2–4 min×1 cycle,

92–95° C.– 1–2 min
32–38° C.– 1–2 min
72° C.– 1.5–2.5 min
} ×30–45 cycles,

72° C.– 4–7 min×1 cycle.

The reaction assay mixture was prepared as set forth below:

| | |
|---|---|
| DNA | 7–20 ng. |
| 10 × buffer | 2–3 ml. |
| $MgCl_2$ | 1.5–2.5 mM. |
| dNTP mix | 150–250 mM. |
| $H_2O$ | As per requirement. |
| Primer | 20–40 ng. |
| Taq. Pool. Enz. | 0.5–2.0 U. |
| | 20–30 $\mu$l reaction. |

The essential oil of the 'RLJCC1' variety has been found to be substantially devoid menthadienols which have previously been reported in the essential oil of *Cymbopogon commutatus*. Also, the essential oil of the new variety has been found to repel mosquitos.

The new 'RLJCC1' variety has not been observed to date under all possible environmental conditions. Thus, it is possible that the phenotype may vary somewhat under different environmental conditions.

SEQUENCE LISTING

<160> NUMBER OF SEQ ID NOS: 3

<210> SEQ ID NO 1
<211> LENGTH: 10
<212> TYPE: DNA
<213> ORGANISM: Artificial Sequence
<220> FEATURE:
<223> OTHER INFORMATION: primer

<400> SEQUENCE: 1 tgccgagctg 10

<210> SEQ ID NO 2
<211> LENGTH: 10
<212> TYPE: DNA
<213> ORGANISM: Artificial Sequence
<220> FEATURE:
<223> OTHER INFORMATION: primer

<400> SEQUENCE: 2 gaaacgggtg 10

<210> SEQ ID NO 3
<211> LENGTH: 10
<212> TYPE: DNA
<213> ORGANISM: Artificial Sequence
<220> FEATURE:
<223> OTHER INFORMATION: primer

<400> SEQUENCE: 3 gggtaacgcc 10

We claim:

1. A new and distinct *Cymbopogon commutatus* plant having the following combination of characteristics:

(a) displays a perennial vigorous growth habit, (b) commonly forms lighter green leaves than typically exhibited by the species, (c) forms an abundance of roots with superior tillering, (d) displays superior drought tolerance, (e) produces essential oil having an enhanced geraniol and geranyl acetate content, and (f) readily undergoes asexual reproduction by the use of slips; substantially as illustrated and described.

* * * * *